United States Patent [19]

Matsumoto et al.

[11] 4,128,580

[45] Dec. 5, 1978

[54] PROCESS FOR THE PRODUCTION OF 1,3-DICHLOROACETONE OXIME AND ITS ACETATE DERIVATIVE

[75] Inventors: Kent E. Matsumoto, Kensington; Jimmy H. Chan, Martinez; Don R. Baker, Orinda, all of Calif.

[73] Assignee: Stauffer Chemical Company, Westport, Conn.

[21] Appl. No.: 751,491

[22] Filed: Dec. 21, 1976

Related U.S. Application Data

[63] Continuation-in-part of Ser. No. 653,797, Jan. 30, 1976, abandoned.

[51] Int. Cl.$^2$ ............................................. C07C 131/00
[52] U.S. Cl. .......................... 260/566 A; 260/566 AE
[58] Field of Search ..................... 260/566 AE, 566 A

[56] References Cited

U.S. PATENT DOCUMENTS

| 3,117,987 | 1/1964 | Horrom | 260/566 AE |
| 3,165,392 | 1/1965 | Koopman | 260/566 AE |
| 3,169,989 | 2/1965 | Tieman et al. | 260/566 AE |
| 3,592,920 | 7/1971 | Gutman et al. | 260/566 AE |

Primary Examiner—Gerald A. Schwartz
Attorney, Agent, or Firm—Joel G. Ackerman

[57] ABSTRACT 1,3-dichloroacetone oxime is prepared from 1,3-dichloropropanone by reaction with a hydroxylamine salt in a strongly acidic medium in the presence of a base selected from the group consisting of tertiary amines, lower alkyl amides, alkali metal bicarbonates, alkali metal carbonates and alkaline earth metal carbonates. 1,3-dichloroacetone oxime acetate is advantageously prepared by reaction of the oxime with acetic anhydride. The acetate is obtained in high purity.

23 Claims, No Drawings

PROCESS FOR THE PRODUCTION OF 1,3-DICHLOROACETONE OXIME AND ITS ACETATE DERIVATIVE

CROSS REFERENCE TO RELATED APPLICATIONS

This application is a continuation-in-part of application number 653,797, filed Jan. 30, 1976 now abandoned.

BACKGROUND AND PRIOR ART

This application relates to an improved process for production of 1,3-dichloroacetone oxime and 1,3-dichloroacetone oxime acetate.

1,3-dichloroacetone oxime, as illustrated in U.S. Pat. No. 3,733,419 of Arnold D. Gutman, is an intermediate for the production of a number of compounds useful in controlling fungi and bacteria. Among these compounds is 1,3-dichloroacetone oxime acetate (compound 5 of the said patent.) According to this patent, the oxime was prepared by reacting 1,3-dichloropropanone with hydroxylamine hydrochloride in the presence of ethanol and water. The oxime was obtained from the reaction products by extraction with chloroform.

Examples of conversion of the oxime to its derivatives, for instance, the trichloroacetate and the crotonate, show that the reaction was conducted between the oxime and an acyl chloride in the presence of benzene and the product recovered from the benzene phase.

When processes of this type were applied to the production of 1,3-dichloroacetone oxime acetate, however, the product turned black either during recovery or subsequently on standing.

It is an object of the present invention to provide an improved process for the production of 1,3-dichloroacetone oxime.

It is a further object of this invention to provide an improved process for the preparation of 1,3-dichloroacetone oxime acetate through the oxime intermediate.

Another object of the present invention is to provide a process for the production of 1,3-dichloroacetone oxime acetate which is comparatively stable and does not discolor on standing.

SUMMARY OF THE INVENTION

In one aspect, this invention comprises a process for the production of 1,3-dichloroacetone oxime comprising reacting 1,3-dichloropropanone with a hydroxylamine salt, establishing the pH of the reaction system at a value of 2 or less and thereafter maintaining the pH of the reaction system at a value of 2 or less throughout the remainder of the reaction.

In another aspect, this invention comprises a process for the production of 1,3-dichloroacetone oxime acetate comprising:

(a) producing 1,3-dichloroacetone oxime by: reacting 1,3-dichloropropanone with a hydroxylamine salt, establishing the pH of the reaction system at a value of 2 or less and thereafter maintaining the pH of the reaction system at a value of 2 or less throughout the remainder of the reaction; and
(b) reacting the 1,3-dichloroacetone oxime from step (a) with acetic anhydride.

DETAILED DESCRIPTION OF THE INVENTION

In producing an oxime by reaction of a ketone with a hydroxylamine salt, it has hitherto been considered that the preferred pH of the system should be between about 4 and 5. See, for instance, Sidgwick, *The Organic Chemistry of Nitrogen*, Clarendon Press (Oxford), 1945, P. 170. Operation at lower pH was felt to result in hydrolysis of the oxime. However, we have now found that, at least for the production of dichloroacetone oxime, optimum and quite unexpected results are obtained by establishing the reaction system in a highly acidic condition, at a pH of 2 or less, and then maintaining the reaction system at a pH of 2 or less throughout the remainder of the reaction.

Operation of the reaction at pH values higher than 2 for the entire reaction time generally results in the formation of a gum or slime.

The hydroxylamine salt may be any of those commonly employed such as hydroxylamine hydrochloride and hydroxylamine sulfate.

In the present process, as well as those heretofore used, it is preferred to conduct the reaction in the presence of an added base. If a sufficient excess of hydroxylamine salt is utilized, this can serve as the base; however, such a practice represents an unnecessary waste of comparatively expensive materials. In general, any suitable base can be used provided it can be readily dispersed throughout the reaction medium without forming undesirable high localized pH values. The alkali metal carbonates and bicarbonates and alkaline earth metal carbonates, particularly calcium carbonate, are the preferred bases for this process. Other members of these groups such as sodium, magnesium, barium, strontium carbonates and sodium and potassium bicarbonates are also suitable. Tertiary amines such as triethylamine, pyridine, substituted pyridines such as the lutidines and dimethylaniline, may also be used.

Lower alkyl amides such as acetamide, formamide and dimethylformamide are also suitable bases for this reaction. However, these are less preferable because although the oxime product can be produced in good yield, it may contain unreacted 1,3-dichloropropanone in a sufficient amount to create problems because of its irritant properites. This compound therefore, must be removed from the oxime product, thereby requiring additional purification steps and equipment.

In general, strong bases such as sodium and potassium hydroxides are not desirable for use in this process as their addition may cause the formation of localized pH values above 2.

The pH may be established at a value of 2 or less by any of several expedients, and may be done by active or passive measures. In general, the pH of the starting reaction mixture of 1,3-dichloropropanone and hydroxylamine salt will be between about 3.7 and about 4. As the reaction proceeds, the pH will drop due to the formation of hydrogen ions as the hydroxylamine salt reacts. Thus, in one embodiment of the process, 1,3-dichloropropanone and the hydroxylamine salt are caused to react and, when the pH drops to below about 2 (generally within 15–45 minutes), addition of the base is commenced. Thereafter, the pH of the reaction mixture is monitored and addition of the base is controlled to maintain the pH at a value no higher than 2. The overall reaction time is generally about 2–4 hours and it is not detrimental to the conduct of the process for the pH of the system to be above 2 for the first 15–45 minutes or so.

In some cases, as was the case in Example 2 which follows, the pH of the initial reaction system may actually be less than about 3.7–4. This is believed to be caused by acidic impurities in the reactants or solvents used in the process, most likely in the hydroxylamine salt. In such a case, the base may be added earlier in the course of the reaction, with pH monitoring and controlled addition of base as above.

An alternate method of operation is to add part of the base at the commencement of the reaction. In such case, there is also added at that time a sufficient quantity of a mineral acid such as hydrochloric, sulfuric, phosphoric or nitric acid to bring the pH of the reaction system down to an initial value of 2 or less. The remainder of the base is subsequently added with pH monitoring and controlled addition to maintain the pH at a value of 2 or less.

In a preferred embodiment, the oxime production step is conducted in the presence of an inert organic solvent, such as benzene, toluene, xylene, chlorinated hydrocarbons such as chloroform, methylene chloride, perchloroethylene, 1,2-dichloroethane and others.

In general, the oxime production step is conducted at temperatures of between about 5° C. and about 85° C., depending on the base and solvent, if used. When using a tertiary amine, lower temperatures are preferred, preferably between about 5° C. and about 40° C., most preferably between about 15° C. and about 25° C. When using an alkaline earth metal carbonate or alkali metal carbonate, the reaction proceeds best at a temperature of between about 35° C. and about 45° C., though higher temperatures up to about 85° C. may be utilized, depending on the boiling point of the solvent.

The reaction of the 1,3-dichloroacetone oxime with acetic anhydride is conducted in the presence of an inert solvent such as those previously mentioned. Small amounts of water may be tolerated so long as a separate aqueous phase is not formed, as the reaction will not proceed to completion in a two-phase system. This step is conducted at a temperature of between about 5° C. and about 40° C. For a complete reaction, acetic anhydride should be used in a slight excess such as about 1.4–1.5 moles per mole of oxime. A smaller excess can be utilized if the organic solution of the oxime is dried prior to its use in the acetate production step.

The oxime may be separated from the reaction mixture before reacting with acetic anhydride. However, in a preferred embodiment, both the oxime production and acetate production reactions are carried out in the presence of the same inert solvent. Since the oxime will be contained in the organic layer from the first reaction, it may be utilized for the next as a solution of oxime in the solvent. Separation of the organic phase of the oxime production step from the aqueous phase should be done carefully to preclude introduction of an undesirable amount of water into the acetate formation system.

The oxime may undergo decomposition if it is allowed to reach a pH of above about 3 or to stand for long periods of time.

In a further embodiment the 1,3-dichloropropanone can be prepared by oxidation of 1,3-dichloropropanol with an oxidizing agent such as sodium dichromate and concentrated sulfuric acid. The 1,3-dichloropropanone can be recovered from the reaction products by extraction with toluene or another suitable solvent and the solution of this compound can be used as one of the starting materials for the oxime production reaction without separation of the ketone. In all steps of the process removal of solvent from a reaction product by evaporation should be performed carefully as all the desired products are quite volatile and substantial amounts may be carried off with the solvents.

The following Examples are presented as illustrative of the invention; however, the invention may comprise conditions and/or variations of the processes not mentioned or outside the ranges of the Examples; therefore, the invention is not intended to be limited thereby, but only by the claims which follow.

EXAMPLE 1

Into a 12-liter flask was introduced 2.5 kg (8.8 mole) sodium dichromate dihydrate and 1 liter of water. The mixture was stirred to dissolve the salt. There was then added 1.94 kg (15.0 mole) of 1,3-dichloro-2-propanol, followed by 2.95 kg (30 mole) of concentrated sulfuric acid dissolved in 0.75 liter of water. The reaction temperature was maintained at about 20° during the course of the reaction and stirring was continued at a moderate rate. Caution was taken as the addition of sulfuric acid to this mixture is quite exothermic. At the end of the reaction, the reaction mixture was viscous and black.

3.3 liters of water and 5.2 liters of toluene were then added to the reaction mixture and the resulting mixture was phase separated. The lower aqueous layer was back extracted with toluene and the combined toluene solutions washed with a small amount of water. The yield of 1,3-dichloropropanone was about 98%.

Into a 12-liter flask was placed the 1,3-dichloropropanone solution in toluene prepared in the previous step, 1.43 kg (8.7 mole) of hydroxylamine sulfate, $(HONH_2)_2 \cdot H_2SO_4$, dissolved in 3 liters of water, and 48 ml of concentrated hydrochloric acid. There was then slowly added while stirring, 1.19 kg (15 mole) pyridine with pH monitoring. The reaction temperature was maintained at 20°–25° C. The pH was maintained at a value of below 2 throughout the addition of the base. The addition was completed in about 2–2.5 hours and the reaction was stirred for 0.5 hours after that time. Gas chromatographic analysis showed that the ketone was completely converted to the corresponding oxime. The reaction products were phase separated, with the oxime being contained in the toluene layer.

The toluene-oxime solution from the previous step was introduced to a 12-liter flask and there was slowly added to it 2.2 kg (21.6 moles) of acetic anhydride. The reaction mixture was maintained at about 20° C. Addition of the anhydride was complete in about 2 hours. After the reaction had been completed 0.5 liters of water were added, the solution was stirred and then phase separated. The toluene layer was washed with saturated sodium bicarbonate solution, dried over magnesium sulfate, filtered and evaporated. The liquid was concentrated in vacuo for 1.5 to 2 hours at about 50° C. There was obtained 2,041 g of 1,3-dichloroacetone oxime acetate, b.p. 80°–82° C. at 4mm Hg pressure. The purity was 95 wt. %; the yield was 74% based on starting 1,3-dichloro-2-propanol and on the intermediate ketone.

EXAMPLE 2

Into a 300 ml flask were introduced a solution of 12.7 g (0.10 mole) 1,3-dichloro-2-propanone in 29.5 ml 1,2-dichloroethane and a solution of 9.5 g (0.058 mole) hydroxylamine sulfate in 20 ml water. The flask was placed in a water bath maintained at 40° C. The initial pH was about 1.5, presumably due to acidic impurities in a reagent or the dichloroethane. After 60 minutes the pH had decreased to a negative value. There was added 2.50 g (0.025 mole) calcium carbonate with another 2.50 g after 30 additional minutes. The pH then increased to about 1.5. The reaction proceeded for a total of 195 minutes, at which point the pH was about 0.8. The reaction product was cooled, filtered and phase separated. The organic phase was placed in a 100 ml flask, to which was added 14.7 g (0.144 mole) acetic anhydride. Temperature was maintained at 40° C. The reaction was 96% complete after 180 minutes: the mixture was then allowed to cool and stand. The resulting solution was stripped under vacuum at 50° C. There was obtained 16.8 g of a light yellow liquid which contained 95.2 weight % (91.3% of theoretical yield) 1,3-dichloroacetone oxime acetate, and 1.3% 1,3-dichloro-2-propanone.

EXAMPLE 3

The oxime was prepared by the process of Example 2 and was isolated. The yield of oxime was 98%; the purity 85–89%.

EXAMPLE 4

The oxime was prepared as in Example 2, with the reaction temperature being maintained at 22° C. The oxime was obtained in 80% yield and 85.1% purity.

EXAMPLE 5

The oxime was prepared as in Example 2 but using only one addition of 2.50 g (0.025 mole) calcium carbonate (about 0.5 mole equivalents per mole-equivalent of hydroxylamine sulfate). The yield of oxime was 73%; the purity 74.1%.

EXAMPLE 6

The oxime was prepared as in Example 2 but a total of 7.50 g (0.075 mole) calcium carbonate was added (about 1.5 mole-equivalents per mole-equivalent of hydroxylamine sulfate). The yield of oxime was 74%; the purity was 79.4%.

What is claimed is:

1. A process for the production of 1,3-dichloroacetone oxime comprising reacting 1,3-dichloropropanone with a hydroxylamine salt in the presence of a base selected from the group consisting of tertiary amines, lower alkyl amides, alkali metal bicarbonates, alkali metal carbonates, and alkaline earth metal carbonates, establishing the pH of the reaction system at a value of 2 or less and thereafter maintaining the pH of the reaction system at a value of 2 or less throughout the remainder of the reaction.

2. A process according to claim 1 in which the base is pyridine.

3. A process according to claim 1 in which the base is sodium carbonate.

4. A process according to claim 1 in which the base is an alkaline earth metal carbonate.

5. A process according to claim 4 in which the base is calcium carbonate.

6. A process according to claim 1 in which the base is an alkali metal bicarbonate.

7. A process according to claim 1 in which the base is added to the reaction system at a time subsequent to the commencement of the reaction and at which the pH of the reaction system is at a value of 2 or less, and the addition of the base is controlled so as to thereafter maintain the pH of the reaction system at a value of 2 or less.

8. A process according to claim 1 in which a portion of the base is added to the reaction system at the commencement of the reaction and the remainder is subsequently added in a controlled fashion so as to maintain the pH of the reaction system at a value of 2 or less, and further comprising simultaneously adding a sufficient quantity of a mineral acid to maintain the pH of the reaction system at a value of 2 or less.

9. A process according to claim 1 in which the temperature is between about 5° C. and about 85° C.

10. A process according to claim 1 in which the reaction is carried out in the presence of an inert organic solvent.

11. A process according to claim 10 in which the solvent is toluene.

12. A process for the production of 1,3-dichloroacetone oxime acetate comprising:
(a) reacting 1,3-dichloropropane with a hydroxylamine salt in the presence of a base selected from the group consisting of tertiary amines, lower alkyl amides, alkali metal bicarbonates, alkali metal carbonates, and alkaline earth metal carbonates, establishing the pH of the reaction system at a value of 2 or less and thereafter maintaining the pH of the reaction system at a value of 2 or less throughout the remainder of the reaction, whereby 1,3-dichloroacetone oxime is produced; and
(b) reacting the 1,3-dichloroacetone oxime from step (a) with acetic anhydride.

13. A process according to claim 12 in which the base is pyridine.

14. The process according to claim 12 in which the base is sodium carbonate.

15. A process according to claim 12 in which the base is an alkaline earth metal carbonate.

16. A process according to claim 15 in which the base is calcium carbonate.

17. A process according to claim 12 in which the base is an alkali metal bicarbonate.

18. A process according to claim 12 in which the base is added to the reaction system at a time subsequent to the commencement of the reaction and at which the pH of the reaction system is at a value of 2 or less, and the addition of the base is controlled so as to thereafter maintain the pH of the system at a value of 2 or less.

19. A process according to claim 12 in which at least a portion of the base is added to the reaction system at the commencement of the reaction and the remainder is subsequently added in a controlled manner so as to maintain the pH of the system at a value of 2 or less, and further comprising simultaneously adding a sufficient quantity of a mineral acid to maintain the pH of the reaction system at a value of 2 or less.

20. A process according to claim 12 in which the acetic anhydride is utilized in step (b) in an excess with respect to the oxime.

21. A process according to claim 12 in which steps (a) and (b) are conducted in the presence of an inert organic solvent.

22. A process according to claim 21 in which the solvent is toluene.

23. A process according to claim 21 in which the oxime is introduced into step (b) as a solution of oxime in an organic solvent obtained from step (a).

* * * * *